United States Patent
Engel et al.

(10) Patent No.: US 7,521,670 B2
(45) Date of Patent: Apr. 21, 2009

(54) STANDARD FOR REFERENCING LUMINESCENCE SIGNALS

(75) Inventors: Axel Engel, Ingelheim (DE); Rainer Haspel, Monsheim (DE); Ute Resch-Genger, Berlin (DE); Katrin Hoffmann, Berlin (DE); Doris Ehrt, Jena (DE); Uwe Kolberg, Mainz (DE); Joseph S. Hayden, Clarks Summit, PA (US); Michael Stelzl, Mainz (DE)

(73) Assignees: Schott AG, Mainz (DE); BAM Bundesanstalt fuer Materialforschung und -pruefung, Berlin (DE)

( * ) Notice: Subject to any disclaimer, the term of this patent is extended or adjusted under 35 U.S.C. 154(b) by 50 days.

(21) Appl. No.: 11/362,587

(22) Filed: Feb. 24, 2006

(65) Prior Publication Data

US 2006/0199018 A1 Sep. 7, 2006

Related U.S. Application Data

(63) Continuation-in-part of application No. 11/210,019, filed on Aug. 23, 2005.

(30) Foreign Application Priority Data

Feb. 25, 2005 (DE) ........................ 10 2005 010 774

(51) Int. Cl.
G01D 18/00 (2006.01)
C09K 11/02 (2006.01)
G01J 1/10 (2006.01)

(52) U.S. Cl. ............................. 250/252.1; 252/301.4 R; 252/301.36; 356/243.1; 501/44; 501/45; 501/47

(58) Field of Classification Search .............. 250/252.1; 252/301.16, 301.4 R, 301.36; 356/243.1, 356/243.4, 243.8; 501/44, 45, 47
See application file for complete search history.

(56) References Cited

U.S. PATENT DOCUMENTS

| 3,773,530 | A | 11/1973 | Morgan |
| 3,935,119 | A * | 1/1976 | Barber et al. ......... 252/301.4 F |
| 4,106,946 | A | 8/1978 | Ritze |
| 4,302,678 | A | 11/1981 | Schiffert |
| 4,798,768 | A * | 1/1989 | Oversluizen et al. ........ 428/426 |
| 6,123,872 | A | 9/2000 | Yamazaki et al. |
| 6,667,259 | B2 | 12/2003 | Clasen et al. |
| 6,770,220 | B1 | 8/2004 | Klimant |
| 2004/0180773 | A1* | 9/2004 | Schreder et al. ................ 501/7 |

(Continued)

FOREIGN PATENT DOCUMENTS

DE 26 21 741 11/1977

(Continued)

*Primary Examiner*—David P Porta
*Assistant Examiner*—Mark R Gaworecki
(74) *Attorney, Agent, or Firm*—Harness, Dickey & Pierce, P.L.C.

(57) ABSTRACT

The invention discloses a standard for referencing luminescence signals, having an optically transparent base material comprising a lanthanum phosphate glass, a fluorophosphate glass, a fluor-crown glass, a lanthanum glass, a glass-ceramic formed therefrom or a lithium aluminosilicate glass-ceramic, the base material including a bulk doping with at least one constituent which is luminescent and comprises at least one rare earth and/or a nonferrous metal, in particular cobalt, chromium or manganese.

11 Claims, 14 Drawing Sheets

U.S. PATENT DOCUMENTS

2004/0212302 A1* 10/2004 Letz et al. .................. 313/512
2005/0054515 A1   3/2005 Kolberg et al.
2005/0253113 A1* 11/2005 Letz et al. ............. 252/301.4 P

FOREIGN PATENT DOCUMENTS

| DE | 101 41 104 C1 | 4/2003 |
| DE | 101 41 101 C1 | 7/2003 |
| DE | 103 11 820 A1 | 9/2004 |
| DE | 10 2004 019 802 A1 | 11/2005 |
| EP | 0 709 345 A1 | 5/1996 |
| EP | 0 926 102 B1 | 6/1999 |
| JP | 08-133780 A | 5/1996 |
| JP | 2000159543 A | 6/2000 |
| WO | WO 03/087424 A1 | 10/2003 |
| WO | WO 03/088340 A2 | 10/2003 |

* cited by examiner

STANDARD FOR REFERENCING LUMINESCENCE SIGNALS

RELATED APPLICATIONS

This is a continuation-in-part application of copending U.S. patent application Ser. No. 11/210,019 claiming priority of German patent application 10 2005 010 774.5 which was filed on Feb. 25, 2005 which is fully incorporated by reference herewith.

BACKGROUND OF THE INVENTION

The invention relates to a standard for referencing luminescence signals and to a process for producing a standard of this type, and also to advantageous applications of a standard of this type.

For the purpose of this disclosure the term luminescence is understood as to include luminescence, fluorescence or both.

In addition to the desired measurement data from the analysis, the results of luminescence measurements also include device-dependent contributions which make it very difficult or virtually impossible to compare luminescence measurement data across device and laboratory boundaries and to achieve long-term comparability. For luminescence measurement data in the spectral region ranging from UV to NIR (near infrared) to be comparable, it is necessary to standardize the spectral parameters and the sensitivity parameters of luminescence measurement systems. Furthermore, the wavelength accuracy and the linearity of the detection systems typically have to be tested. Defined reference systems, such as for example luminescence standards, are required to solve this problem. The standardization of the spectral characteristics of luminescence measurement systems may take place independently of the standardization of the sensitivity parameters, which requires either luminescence intensity standards or absolute measurements of the luminescence intensity or of the luminescence quantum yield. As an alternative to physical transfer standards, such as for example receiver standards for determining the wavelength dependency of the spectral illumination intensity of the excitation channel of standard lamps or radiance standards for determining the wavelength dependency of the spectral sensitivity of the emission channel, it is also possible for chemical transfer standards, or what are known as luminescence standards, to be used for the spectral characterization of luminescence measurement systems. In this context, for the standardization of the spectral characteristics of luminescence measurement systems it is sufficient to use spectral luminescence standards with "technical" luminescence spectra corrected (for device-specific influences), given as relative or standardized luminescence intensities, attributable to the primary radiometric standard "black beam" and/or cryoradiometer.

In addition to spectral standards and intensity standards, standards which are simple to handle and have as high a long-term stability as possible are required for the characterization and testing of the wavelength accuracy, for the characterization of the day-to-day performance and for the recording of the device ageing (spectral effects and sensitivity). The demands which are imposed on standards for the referencing of luminescence signals (referred to below as "luminescence standards") include, depending on the particular application area, inter alia depending on the composition, luminescence in the UV to NIR spectral region, luminescence spectra which are as unstructured and wide as possible for spectral standards, a high and known purity, the minimum possible overlap between absorption and emission spectra;

a wavelength-independent quantum yield of the luminescence (in the spectral region used for the device characterization), an isotropic emission, a low variation in the intensity at a statistically relevant number of measurement points, i.e. a high homogeneity, a temperature dependency of the luminescence which is as low as possible and/or known in the relevant ambient temperature range, luminescence lives in the nanosecond, microsecond or millisecond range (for lifetime standards), as many narrow bands as possible in the UV to NIR spectral region (for wavelength standards, day-to-day performance, long-term stability, intensity standards), a known and sufficient long-term stability (thermal and photochemical), a high reproducibility in the case of single-use standards, the possibility of measuring sample and transfer standard under identical measurement conditions (for example including identical measurement parameters and measurement geometry, sample formats, such as cuvette, slide, microtiter plate), at comparable signal intensities/photon counting rates, with emission characteristics that are as similar as possible.

To make luminescence properties, which are generally measured in arbitrary and relative units, comparable, in the prior art luminescence standards are known, but in may cases these standards do not have a sufficient long-term stability, homogeneity or isotropy, or else they comprise toxic or environmentally harmful materials, such as for example cadmium or uranium.

For example, U.S. Pat. No. 4,302,678 discloses a standard for the calibration of a system which scans in the UV region and is used for the detection of surface defects on workpieces. The standard consists of a yellow potassium borosilicate glass which comprises uranium oxide. The use of uranium oxide is regarded as disadvantageous on account of the associated safety measures required and also problems of environmental protection. Furthermore, a standard of this type does not have the required photostability and long-term stability.

U.S. Pat. No. 6,770,220 discloses standards for the referencing of fluorescence signals which include sol-gel glasses, other glasses or polymers incorporating luminescent microparticles or nanoparticles. These are in particular luminescent nanoparticles of polymers and metal-ligand complexes of ruthenium, osmium, rhenium, iridium, platinum or palladium.

U.S. Pat. No. 6,123,872 discloses a luminescent glass with a long-lasting afterglow which can be used as night illumination or a night signal or as a material for confirming an infrared laser or the like. This is an oxide glass which, when excited by radiation such as gamma rays, X-rays or UV-rays, can have a long-lasting afterglow and photostimulated luminescence, the glass comprising from 1 to 55% by weight of $SiO_2$, from 1 to 50% by weight of $B_2O_3$, from 30 to 75% by weight of ZnO, further optional constituents and terbium or manganese as fluorescent agent.

However, a glass of this type cannot be used as a luminescence standard.

A range of colored glasses which can be used as steep edge filters are known as filter glasses. These include U.S. Pat. No. 6,667,259 which discloses an optical colored glass for a steep edge filter which may comprise from 30 to 75% by weight of $SiO_2$, 5 to 35% by weight of $K_2O$, 0 to 5% by weight of $TiO_2$, 4 to 7% by weight of $B_2O_3$, 5 to 30% by weight of ZnO, 0.01 to 10% by weight of F and 0.1 to 3% by weight of copper, silver, indium, gallium, aluminium, yttrium, sulphur, selenium or tellurium. This is a colored flash glass in which the coloration is produced by colloidal precipitation of semiconductor compounds during cooling of the melt or by subsequent heat treatment.

Further colored glasses of a similar type are known from U.S. patent application US 2005/0054515 A1 and from U.S. Pat. No. 4,106,946.

U.S. Pat. No. 3,773,530 discloses a further colored glass for a filter, which comprises cadmium sulphide as coloring constituent.

The photostability of colored glasses of this type is not sufficient to allow them to be used as luminescence standards.

Luminescence standards with fluorescent polymer layers on a non-fluorescent support are known from WO 02/077620 A1.

WO 01/59503 A2 discloses a luminescence standard having a substrate, for example made from quartz, to which a patterned surface of fluorescent material is applied.

DE 202004002064 U1 discloses a microarray support, which includes a substantially non-fluorescent substrate as support and at least one standard for fluorescence measurements which includes a colored glass. The colored glass comprises semiconductor compounds, which may be cadmium-semiconductor compounds or copper-, silver, indium-, gallium-, aluminium-, sulphur- or selenium-semiconductor compounds. The colored glasses comprise 30 to 75% by weight of $SiO_2$, 5 to 35% by weight of $K_2O$, 0 to 5% by weight of $TiO_2$, 0.01 to 10% by weight of fluorine and 0.01 to 3% by weight of $M'M'''Y''_2$, where M' is $Cu^+$ and/or $Ag^+$, M''' is $In^{3+}$ and/or $Ga^{3+}$ and/or $Al^{3+}$ and Y'' is $S^{2-}$ and/or $Se^{2-}$. The fluorescent semiconductor compounds are in the form of colloidal nanocrystals distributed through the glass.

Furthermore, however, there is a need for standards which are distinguished by a particularly high quality, i.e. in particular have a high homogeneity and isotropy, a low temperature dependency and a good long-term stability and photostability. Standards of this type could also satisfy further requirements, such as for example checking of the spectral sensitivity and wavelength accuracy. The time axis in time-resolved luminescence measurements should also be checked.

The colored glasses which are known in the prior art have proven not to satisfy these requirements, since they are not photostable. The other luminescence standards which are known in the prior art are also not of sufficient quality.

SUMMARY OF THE INVENTION

It is a first object of the invention to disclose a standard for referencing luminescence signals (a luminescence standard) which as far as possible avoids the drawbacks of the prior art and is of as high a quality as possible.

It is a second object of the invention to disclose a method for producing a standard of this type and an advantageous application for a standard of this type.

It is a third object of the invention to disclose a luminescence standard which can be used in the UV to NIR spectral range.

It is a forth object of the invention to disclose a luminescence standard which is of a high and known purity.

It is a fifth object of the invention to disclose a luminescence standard having a minimum possible overlap between absorption and emission spectra.

It is a sixth object of the invention to disclose a luminescence standard having a wavelength-independent quantum yield of the luminescence (in the spectral region used for the device characterization).

It is a seventh object of the invention to disclose a luminescence standard having an isotropic emission and a low variation in the intensity at a statistically relevant number of measurement points, i.e. a high homogeneity.

It is an eighth object of the invention to disclose a luminescence standard having a temperature dependency of the luminescence which is as low as possible and/or known in the relevant ambient temperature range.

It is a ninth object of the invention to disclose a luminescence standard having a luminescence live in the nanosecond, microsecond or millisecond range.

It is a tenth object of the invention to disclose a luminescence standard having as many narrow bands as possible in the UV to NIR spectral region.

It is a further object of the invention to disclose a luminescence standard having a known and sufficient long-term stability (thermal and photochemical).

It is a further object of the invention to disclose a luminescence standard having a high reproducibility (single-use standard).

It is a further object of the invention to disclose a luminescence standard providing the possibility of measuring sample and transfer standard under identical measurement conditions (for example including identical measurement parameters and measurement geometry, sample formats, such as cuvette, slide, microtiter plate), at comparable signal intensities/photon counting rates, with emission characteristics that are as similar as possible.

These and other objects of the invention are achieved by a standard for referencing luminescence signals, having an optically transparent base material comprising a lanthanum phosphate glass, a fluorophosphate glass, a fluor-crown glass, a lanthanum glass, a glass-ceramic formed therefrom or a lithium aluminosilicate glass-ceramic, the base material comprising a bulk doping with a rare earth and/or a non-ferrous metal, in particular cobalt, chromium or manganese, which is fluorescent or luminescent.

In this way, the object of the invention is entirely achieved.

A luminescence standard according to the invention is distinguished by a particularly good homogeneity, isotropy, long-term stability and photostability.

On account of its high quality, the luminescence standard according to the invention can be used for a very wide range of applications. By way of example it can be used as a luminescence standard for characterizing the long-term stability of luminescence measurement systems. It can also be used as a wavelength standard, as a luminescence intensity and luminescence lifetime standard for the spectral region from UV to NIR and for comparability and standardization of luminescence measurement data. In this context, statements can be made as to any change in the spectral sensitivity of the detection system and of the wavelength accuracy, as to the determination and characterization of the wavelength accuracy, as to the calibration of luminescence intensities and as to the characterization and calibration of luminescence measurement systems with time-resolved luminescence detection in the UV to NIR spectral region. Furthermore, the standard according to the invention is suitable as a reference system or standard for characterization of the (intrinsic) luminescence of materials in the UV to NIR spectral region from 250 to 1700 nm.

The lifetime/decay times can be "set" by stipulating the base material, by the concentration of the doping and by redox processes.

The absorption and emission effect cross sections can be varied within wide limits, in particular if a glass-ceramic is used as base material.

Unlike with colored glasses known in the prior art, the crystallites in the glass-ceramic according to the invention (for example doped Robax®) are >10 nm. In the standard according to the invention, the luminescent dopant is not incorporated colloidally, as in the case of standards known in the prior art.

If dopants including nonferrous metals are used, wide, unstructured emission bands result, and the standards can be applied all the way into the NIR region (for example in the case of dopings with $Cr^{3+}$). The prior art has not hitherto disclosed a spectral fluorescence standard for the NIR region.

If dopants comprising rare earths are used, sharp line spectra result, which can be used, for example, for wavelength calibration and/or for checking the wavelength accuracy and for determining the spectral resolution of luminescence measurement systems.

The luminescence standards according to the invention can be produced for various measurement geometries and formats, i.e. for example in cuvette form, in slide form as microplates and in other forms.

The fluorescence intensity can be influenced in a suitable way by varying the dopant concentration.

According to a further configuration of the invention, the base material is a lanthanum phosphate glass which comprises 30 to 90% by weight of $P_2O_5$, preferably 50 to 80% by weight, particularly preferably 60 to 75% by weight of $P_2O_5$, as well as standard quantities of refining agents.

Furthermore, the lanthanum phosphate glass may comprise 1 to 30% by weight of $La_2O_3$, preferably 5 to 20% by weight, particularly preferably 8 to 17% by weight of $La_2O_3$.

Furthermore, the base material preferably comprises 1 to 20% by weight of $Al_2O_3$, preferably 5 to 15% by weight of $Al_2O_3$, and 1 to 20% by weight of $R_2O$ (alkali metal oxide), which may preferably be 1 to 20% by weight of $K_2O$, preferably 5 to 15% by weight of $K_2O$.

According to a further configuration of the invention, the base material is doped with $Cr_2O_3$, preferably with 0.01 to 5% by weight, particularly preferably with 0.02 to 2% by weight of $Cr_2O_3$.

According to a further configuration of the invention, the base material is doped with $Ce_2O_3$, $Eu_2O_3$, $Tb_2O_3$ and/or $Tm_2O_3$.

If the base material is a fluorophosphate glass, this material preferably comprises from 5 to 40% by weight of $P_2O_5$, and a fluoride content of from 60 to 95% by weight.

A base material of this type is preferably doped with 0.01 to 5% by weight, preferably with 0.05 to 2% by weight, of $Er_2O_3$ and/or $Eu_2O_3$.

By way of example, the base material may in this case be doped with from 0.05 to 0.3% by weight of $Er_2O_3$ and 0.5 to 2% by weight of $Eu_2O_3$, preferably with approximately 0.1% by weight of $Er_2O_3$, and approximately 1% by weight of $Eu_2O_3$.

Furthermore, according to the invention the base material may be optical fluor-crown glasses, in particular FK52 or FK51 (Schott trade names), or a lanthanum glass, in particular LAK-8 (Schott trade name).

In this case, the base material may, for example, be an optical glass which comprises 0.5 to 2% by weight of $La_2O_3$, 10 to 20% by weight of $B_2O_3$, 5 to 25% by weight of $SiO_2$, 10 to 30% by weight of SrO, 2 to 10% by weight of CaO, 10 to 20% by weight of BaO, 0.5 to 3% by weight of $Li_2O$, 1 to 5% by weight of MgO, 20 to 50% by weight of F, as well as standard quantities of refining agents.

If the base material is in the form of lanthanum glass, it may, for example, comprise 30 to 60% by weight of $La_2O_3$, 30 to 50% by weight of $B_2O_3$, 1 to 5% by weight of $SiO_2$, 1 to 15% by weight of ZnO, 2 to 10% by weight of CaO and standard quantities of refining agents.

Fluor-crown glasses or lanthanum glasses of this type are preferably doped with from 3 to 100 ppm of nonferrous metals, preferably of cobalt, chromium and/or manganese.

Furthermore, the base material used may be a glass-ceramic, in particular a lithium aluminosilicate glass-ceramic, such as for example the transparent glass-ceramics Robax® (Schott-Internal designation 87213) or Cleartrans® (Schott-Internal designation 87233). For this purpose, it is preferable to use a dopant which comprises $Eu_{O3}$, $Er_2O_3$ and/or $Sm_2O_3$.

In this case, it is particularly preferred that the dopant comprises 0.1 to 5% by weight of $Eu_2O_3$, 0.01 to 0.5% by weight of $Er_2O_3$ and/or 0.1 to 2% by weight of $Sm_2O_3$.

In a preferred refinement of the invention, the base material is produced from raw materials which comprise at most 100 ppm of rare earths.

Furthermore, the base material preferably has a water content of less than 0.1% by weight, preferably of less than 0.01% by weight.

This allows quenching and extinction effects to be ruled out.

According to a further development of the invention, the standard according to the invention can be designed as a self-supporting body, i.e. in particular in cuvette format (preferably 12×12×50 mm or smaller), in the microtiter plate format and specimen slide format (preferably 75×25×1 mm or smaller) or as a capillary.

In addition, it is fundamentally also possible, for special applications, to produce a standard according to the invention having a substrate formed from a material which is substantially non-luminescent, to which the base material comprising the dopant is applied.

In this case, the base material with the dopant can be formed as a continuous coating on the substrate.

On the other hand, it is also possible to apply the base material with the dopant to the substrate as a patterned coating.

Standards of this type, having a substrate comprising a material which is non-luminescent and with a coating of an optically transparent base material of glass or glass-ceramic which includes a dopant with at least one constituent that is luminescent, can be produced by vaporizing the base material together with the dopant and by depositing both together on the substrate.

In this case, the base material with the dopant can be used as a target which is locally vaporized by means of an electron beam and deposited on the substrate.

If it is desired to form a patterned coating, the substrate can be provided, prior to the deposition operation, with a masking which is at least partially removed again after the coating operation, as is fundamentally known from CA 2479823 A1 (WO 03/088340 A2) which is fully incorporated by reference.

In this case, the vaporization and deposition may be plasma ion assisted.

The process for vaporizing and depositing the doped base material on a substrate surface is not restricted to the materials mentioned above, but rather can in principle also be carried out for other standards consisting of any suitable materials.

It will be understood that the features of the invention mentioned above and those which are yet to be explained below can be used not only in the combination described in each instance, but also in other combinations or as stand-alone features without departing from the scope of the invention.

BRIEF DESCRIPTION OF THE DRAWINGS

Further features and advantages of the invention will emerge from the following description of preferred exemplary embodiments with reference to the drawings, in which.

DETAILED DESCRIPTION OF THE PREFERRED EMBODIMENTS

EXAMPLE 1

The compositions of various lanthanum phosphate glasses which are individually doped with $Cr_2O_3$ or are multiply doped with rare earth ions, are summarized in Table 1.

TABLE 1

| | % by weight | % by weight | % by weight | % by weight | % by weight |
| | | | Specimen | | |
| OXIDE | A | B | C | D | E |
| --- | --- | --- | --- | --- | --- |
| $Al_2O_3$ | 8.498 | 8.774 | 8.857 | 8.498 | 8.498 |
| $P_2O_5$ | 68.378 | 70.593 | 71.267 | 68.378 | 68.378 |
| $K_2O$ | 9.316 | 6.328 | 6.388 | 9.316 | 9.316 |
| $La_2O_3$ | 13.808 | 14.256 | 10.669 | 13.808 | 13.808 |
| $Ce_2O_3$ | | | 0.126 | 0.13 | 1.21 |
| $Eu_2O_3$ | | | | 1.24 | 1.23 |
| $Tb_2O_3$ | | | 2.693 | 2.63 | 2.62 |
| $Cr_2O_3$ | | 0.050 | | | |
| $Tm_2O_3$ | | | | | 1.02 |

EXAMPLE 2

Fluorophosphate glasses (FP-glasses) which have a $P_2O_5$ content of 5 to 40% by weight and a fluoride content of 60 to 96% by weight are used. Individual dopings of approximately 0.1% by weight of $Er_2O_3$ and approximately 1% by weight of $Eu_2O_3$ are used.

One FP-glass used as a lifetime or decay standard had the following composition (in mol-%):
35% $AlF_3$
20% $CaF_2$
15% $SrF_2$
10% $MgF_2$
10% $Sr(PO_3)_2$ The glass was doped with 5 wt.-% of $Er_2O_3$.

EXAMPLE 3

Optical fluor-crown glasses FK-52, FK-53 and glass LAK-8 are doped with nonferrous metals, specifically in the range between 3 and 100 ppm with cobalt, chromium and/or manganese.

The result is a wide-band emission (420<λ<850 nm) in the excitation range from 400 to 750 nm which is of relevance to bioanalysis. The compositions of the fluor-crown glasses FK51 and FK52 and of the lanthanum glass LAK-8 are given in Table 2.

TABLE 2

| Oxide | % by weight | % by weight |
| --- | --- | --- |
| Glass | FK51/FK52 | LAK-8 |
| $La_2O_3$ | 0.5-2% | 30-60% |
| $B_2O_3$ | 10-20% | 30-50% |
| $SiO_2$ | 5-25% | 1-5% |
| SrO | 10-30% | |
| CaO | 2-10% | 2-10% |
| BaO | 10-20% | |

TABLE 2-continued

| Oxide | % by weight | % by weight |
|---|---|---|
| Li$_2$O | 0.5-3% | |
| MgO | 1-5% | |
| F | 20-50% | |
| ZnO | | 1-15% |

EXAMPLE 4

A lithium-aluminium glass-ceramic (LAS glass-ceramic) is doped with rare earths. In particular the LAS glass-ceramic marketed by Schott under the trademark Ceran® can be used for this purpose. In this case, by way of example, approximately 0.1 to 5% by weight of Eu$_2$O$_3$, 0.01 to 0.5% by weight of Er$_2$O$_3$ and/or 0.1 to 2% by weight of Sm$_2$O$_3$ can be added.

The results of various tests aimed at demonstrating the photostability, homogeneity and anisotropy of various glasses according to the invention are explained in more detail below with reference to FIGS. 1 to 6.

Figure 1:
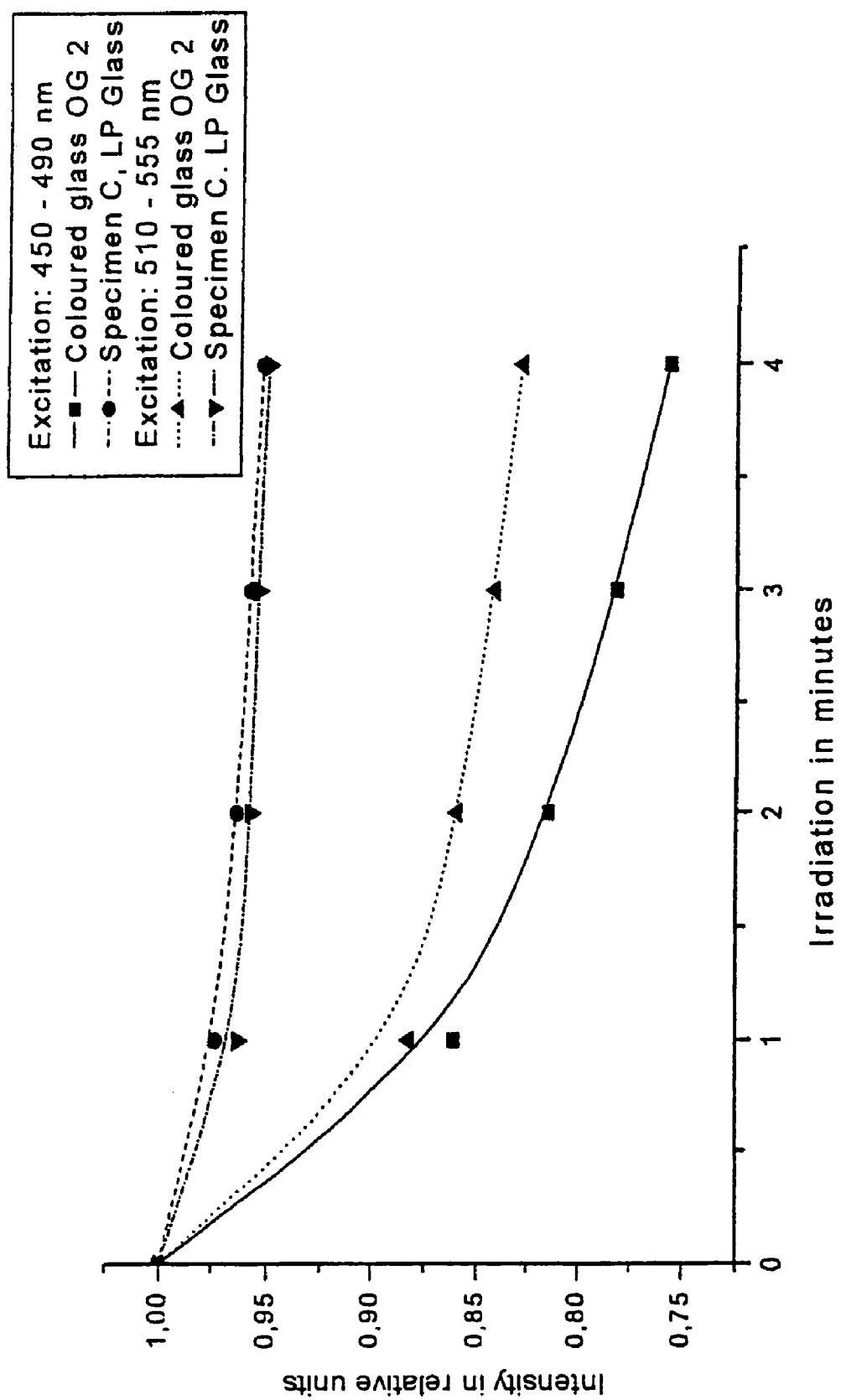
FIG. 1 shows the results of an irradiation test carried out on a glass according to the invention compared to a conventional colored glass, in which the intensity is plotted against the irradiation time.

FIG. 1 shows the demonstration of the photostability carried out on glass C from Table 1 compared to the conventional colored glass OG2 (52% by weight of SiO$_2$, 22.5% by weight of K$_2$O, 3.9% by weight of B$_2$O$_3$, 19.5% by weight of ZnO, 1.2% by weight of CdS, 0.63% by weight of Na$_2$SeO$_3$ and 0.1% by weight of Cd).

Irradiation was carried out using a Xenon lamp in the spectral regions 450 to 490 and 510 to 555 nm.

Whereas the lanthanum phosphate glass according to the invention with rare earths doping has an intensity drop of less than 5% even after an irradiation time of 4 minutes, the conventional colored glass OG2 has a considerable drop in intensity even after a short time.

Figure 2:
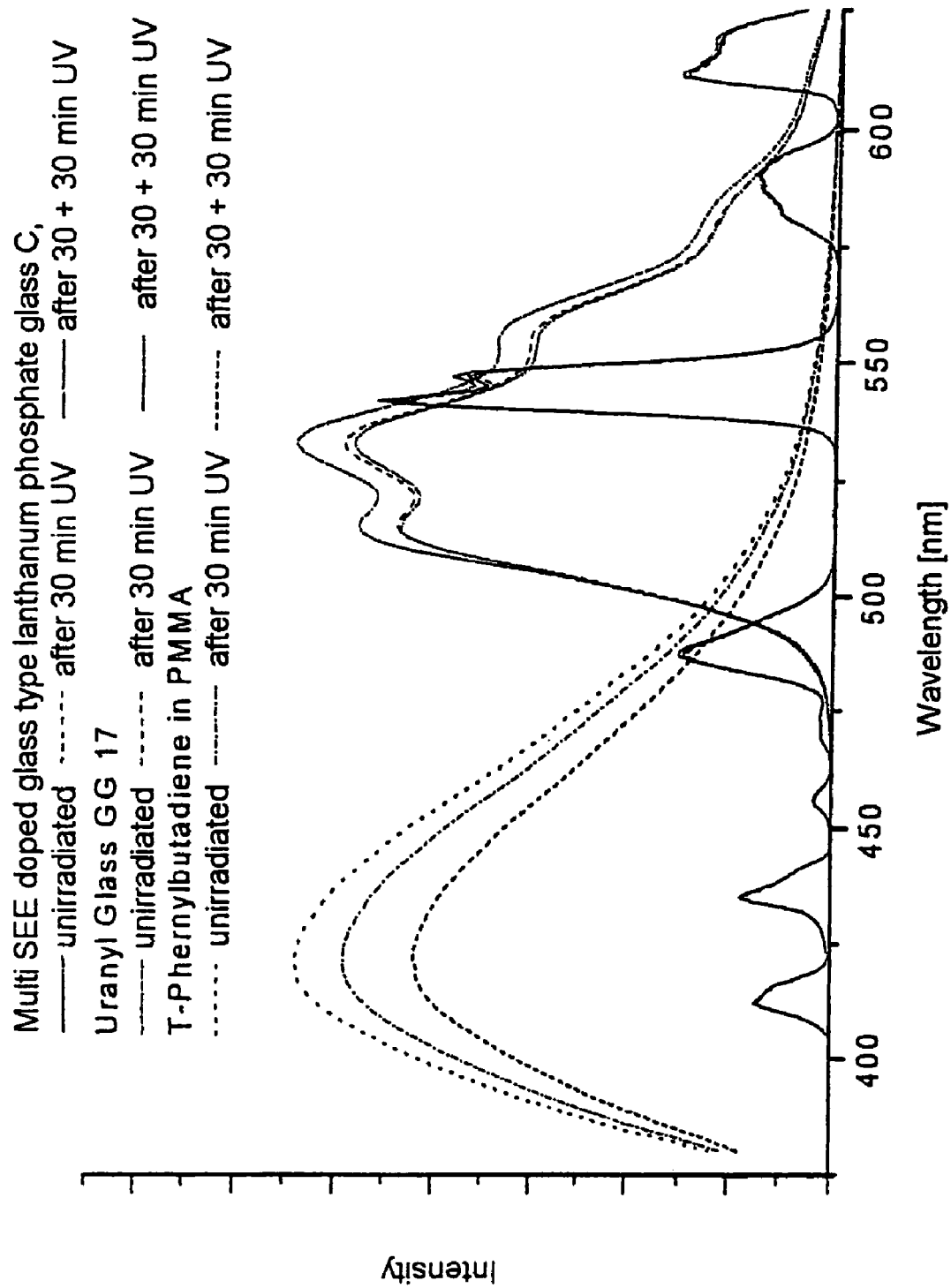
FIG. 2 shows the emission spectra of a lanthanum phosphate glass according to the invention which is doped with a plurality of rare earths, compared to a conventional Uranyl glass and conventional T-phernylbutadiene in PMMA, in each case without irradiation, after irradiation with UV for 30 minutes and after irradiation with UV for 60 minutes, with the intensity in arbitrary units plotted against the wavelength in nanometers.

FIG. 2 shows the results of irradiation with a low lamp HOK-4, which emits at 365 nm, with subsequent excitation at 365 nm. The multiply rare earth doped lanthanum phosphate glass C (Table 1) and a Uranyl Glass GG17 and a T-phernylbutadiene in PMMA are shown for comparison purposes. The intensity measured is plotted in arbitrary units against the wavelength.

It can be seen from the illustration that the polymeric fluorescent material comprising T-phernylbutadiene in PMMA reveals a considerable drop in intensity after irradiation (cf. maximum at 425 nm). The Uranyl glass GG17, the maximum of which is approx. 540 nm, also has a noticeable drop in intensity after irradiation, i.e. is not photostable.

The standard according to the invention (specimen C according to Table 1) reveals a series of pronounced intensity maxima at approx. 415, 435, 480, 550, 580 and approximately 620 nm. Scarcely any intensity differences are discernible between the unirradiated state and the state after 30 or 60 minutes of irradiation.

Figure 3:
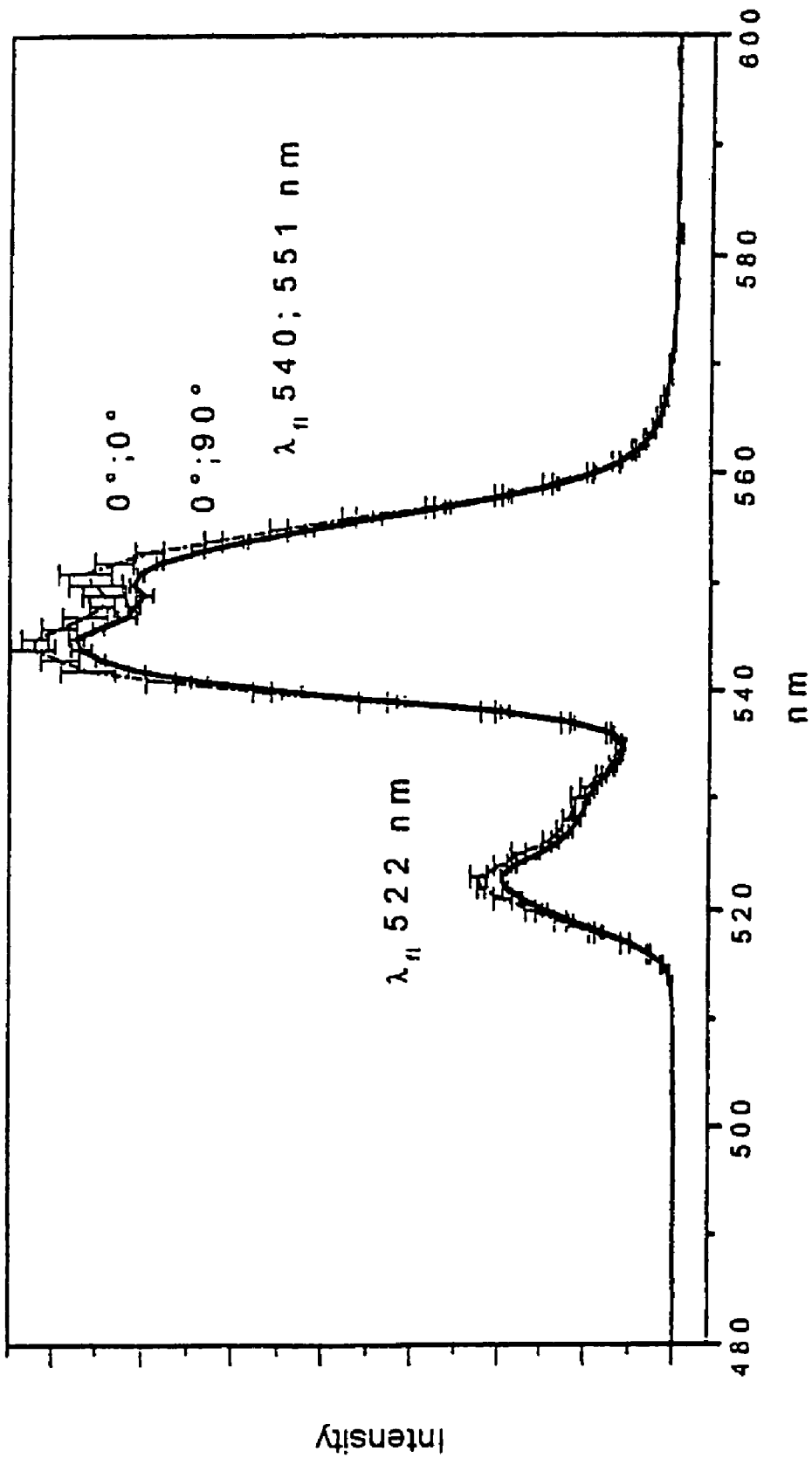
FIG. 3 shows the result of measurements for the detection of the good homogeneity and anisotropy carried out on a fluorophosphate glass according to the invention which is doped with 1% of erbium oxide, with the intensity plotted against the wavelength.

FIG. 3 shows the result of the anisotropy and homogeneity test carried out on a fluorophosphate glass with an individual doping of approximately 1% by weight of Er$^{3+}$. The glass composition was as follows (in mol. %): 35% AlF$_3$, 15% SrF$_2$, 30% CaF$_2$, 10% MgF$_2$, 20% P$_2$O$_5$.

The excitation took place at 378 nm, and measurement was carried out at 0° (reflection) and 900°. The measurement was background- and spectrum-corrected. The homogeneity was tested on the basis of four measurement points (N=4). The plotting of the intensity (in arbitrary units) against the wavelength uses the error bars to demonstrate that overall the anisotropy is very low (0.02732) and the homogeneity is very good. The illustration additionally indicates the measured wavelength maxima at 522, 540 and 551 nm.

Figure 4:
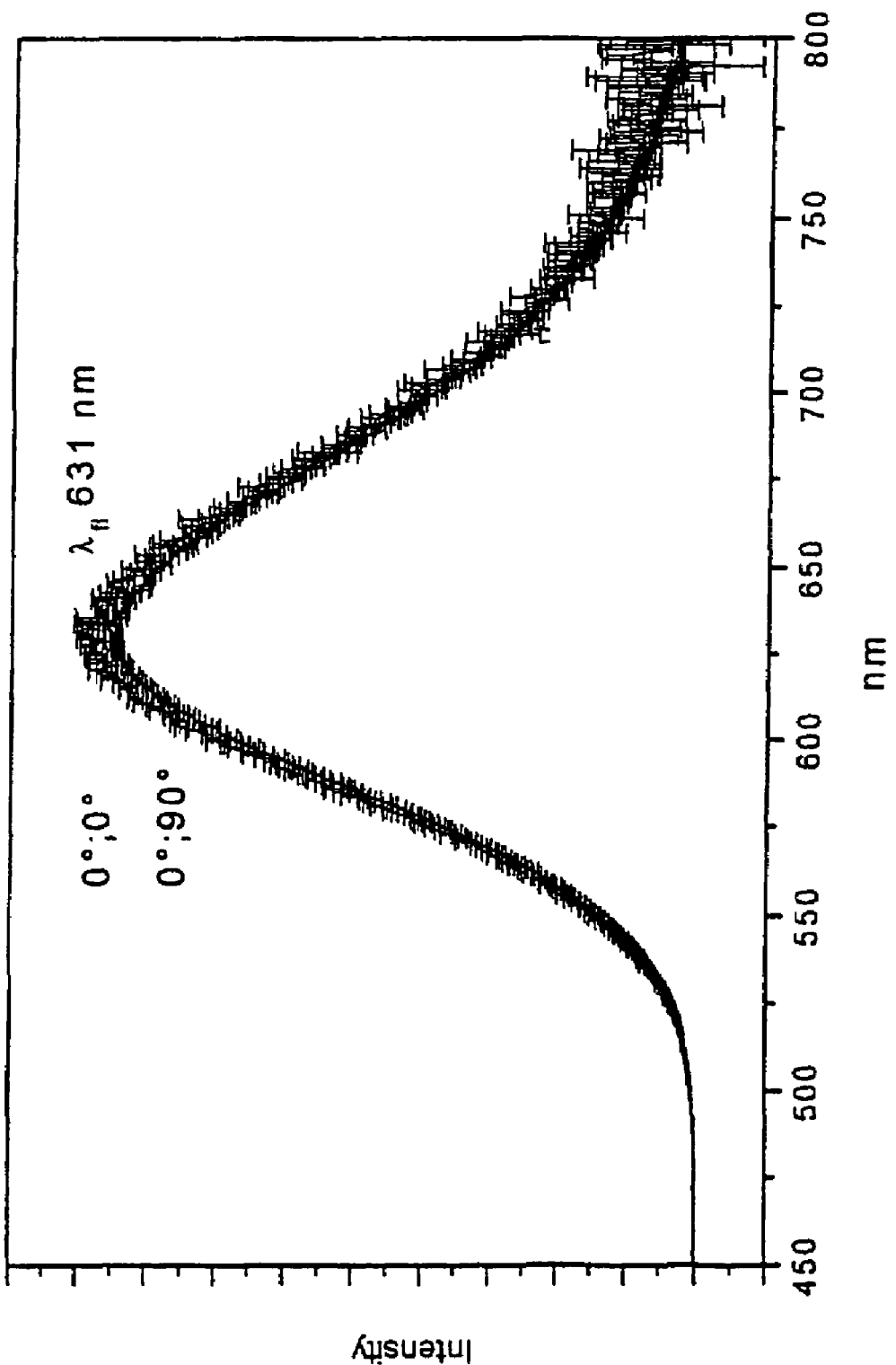
FIG. 4 shows a diagram corresponding to FIG. 3 of a fluorophosphate glass which is doped with 1% by weight of $Eu_2O_3$, with the intensity again plotted against the wavelength.

FIG. 4 shows a corresponding testing of the homogeneity and anisotropy of a fluorophosphate glass which is doped with 1% by weight of Eu$^{3+}$. The excitation was carried out at 404 nm. Measurement was carried out at 0° and 90° (reflection). The measurement was background- and spectrum-corrected. The anisotropy was determined as 0.01407. The homogeneity was tested at four measurement points.

Once again, a very good anisotropy and homogeneity were found.

Figure 5:
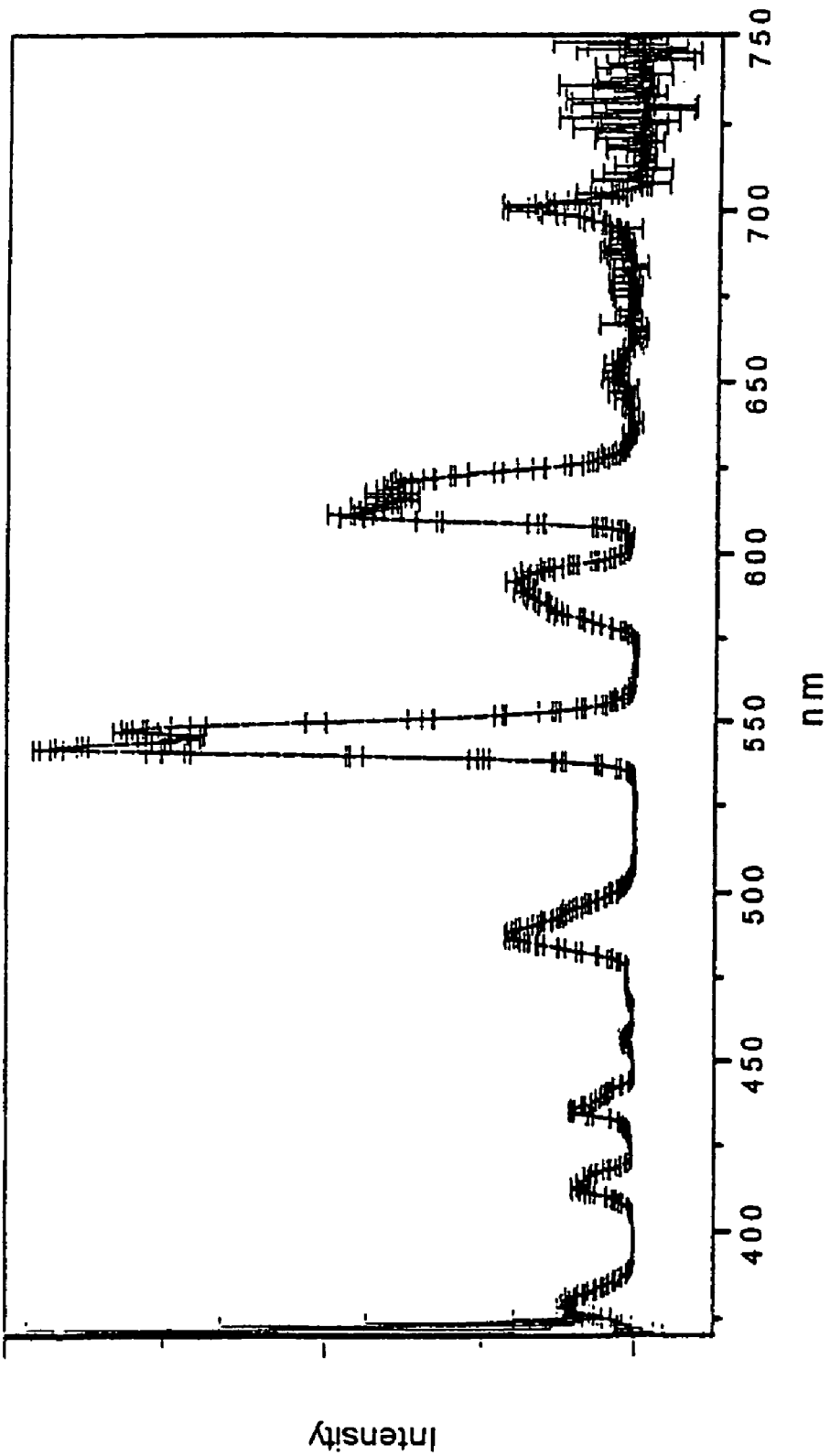
FIG. 5 shows an illustration corresponding to FIG. 3 for demonstrating the good anisotropy and homogeneity properties of a lanthanum phosphate glass which is doped with $Eu_2O_3$.

FIG. 5 shows a corresponding testing of a lanthanum phosphate glass corresponding to specimen C (cf. Table 1). The excitation took place at 365 nm. Measurement was carried out at 0° and 90° (reflection). The measurement was background- and spectrum-corrected. The anisotropy was determined as 0.00783. The homogeneity was tested at four measurement points.

In this case too, a very low anisotropy and a very good homogeneity were found.

Figure 6:
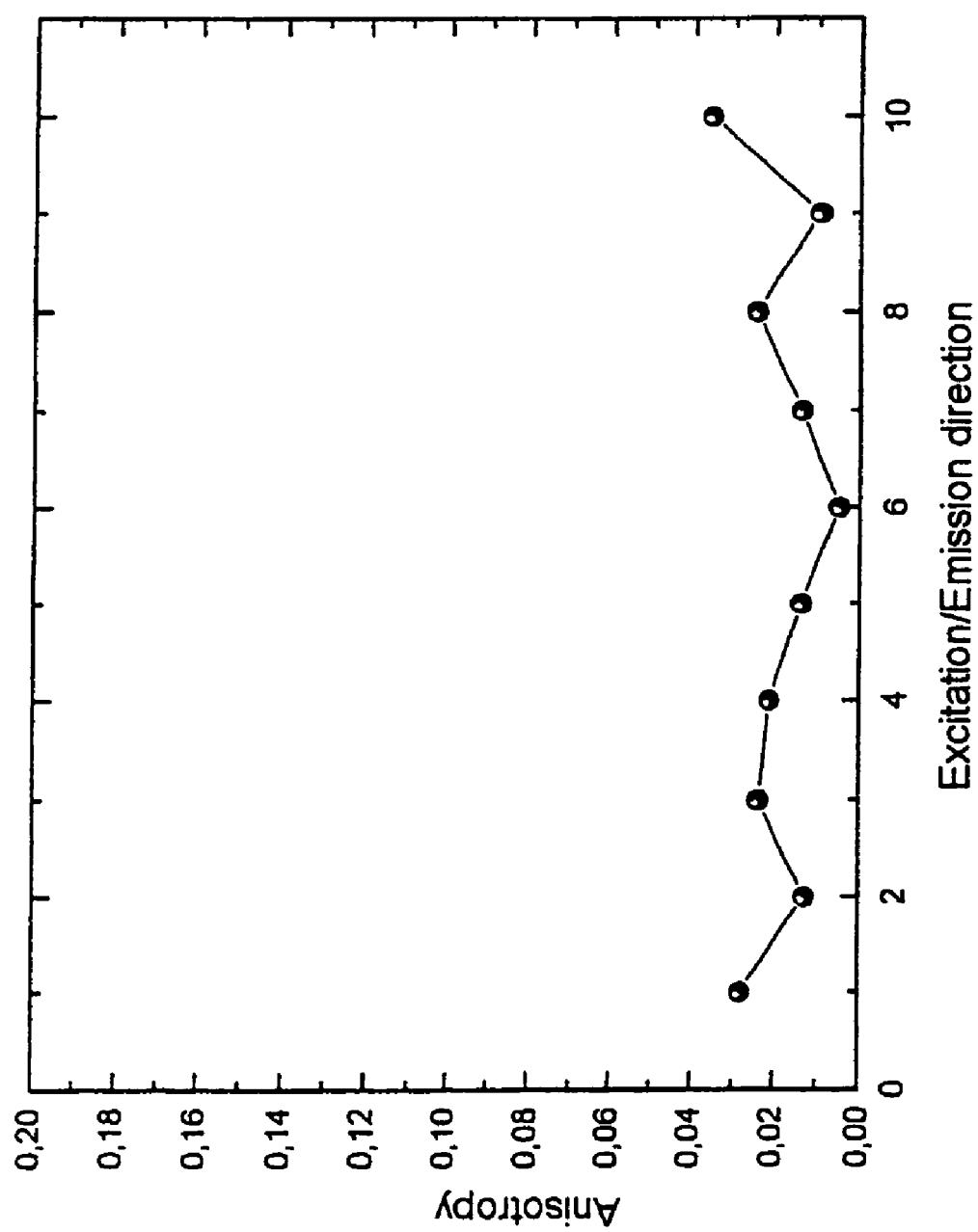
FIG. 6 shows the results of measurements for testing the anisotropy of the glass shown in FIG. 5.

FIG. 6 shows the measurement of the anisotropy on the lanthanum phosphate glass specimen C (cf. Table 1) as a function of the excitation/emission direction. In this case, the measurements were carried out as follows: Measurements took place at 0° (normal situation) and 90°. The emission was measured at 0° (measurement point 1) or 90° (measurement point 3) and at 0° (measurement point 2) or 180° (measurement point 4), respectively. In addition, measurements were carried out at various height positions of the specimen (measurement points 5 and 7, and 6 and 8, respectively). Measurement points 9 and 10 represent the anisotropy measurements for the 0-180° arrangement, i.e. in transmission. The anisotropy values are then given (in arbitrary units) relative to the conventional 0-90° arrangement (excitation/emission).

This again demonstrates a very good isotropy of the material tested.

The standards according to the invention can be produced substantially by processes which are known to the person skilled in the art, in which particularly pure starting materials (less than 100 ppm of rare earths) are used and the glasses are melted "dry", so that the water content is preferably less than 0.01% by weight.

The luminescent or fluorescent constituents (fluorophores) used can be supplied to the base material in the form of oxides or fluorides during the melting of the glass.

The known production processes begin with the melting of the glass composition (comprising the steps of melting down the batch, refining, homogenizing and conditioning). The melting-down takes place in ceramic crucibles at temperatures from approximately 1100 to approximately 1550° C., preferably in the range from approximately 1200 to 1360° C. The melting until seed-free (refining) is preferably carried out at a slightly lower temperature, for example at approximately 1200 to 1400° C. After a standing phase, the temperature is lowered in the usual way in order to homogenize the melt. Casting typically takes place into a suitable mould at between approximately 950 and 1050° C.

If a lithium-aluminosilicate (LAS) glass-ceramic is used, a heat treatment which is known for glass-ceramics of this type is carried out for nucleation and subsequent ceramization.

If the quality demands are particularly high, the melting can be carried out in platinum crucibles or ceramic crucibles lined with platinum, in order to secure a particularly high purity.

If a base material which has been volume-doped in accordance with the invention is to be deposited as a coating on a support which is substantially non-luminescent, evaporation and subsequent deposition can be carried out, as is fundamentally known from Canadian patent application CA 2479823 A1 (WO 03/088340 A2) and from Canadian patent application CA 2480691 (WO 03/087424 A1) which are fully incorporated by reference herewith.

To do this, it is possible to use an electron beam generator with a radiation deflection device and a glass target onto which an electron beam is directed. At the location where the electron beam impinges on the target, the glass is vaporized and is then precipitated on the substrate that is to be coated. To enable the glass of the target to be vaporized as uniformly as possible, the target is rotated and the electron beam executes a scanning motion. In addition the arrangement may also comprise a plasma source for the generation of an ion beam which, in operation, is directed onto the side that is to be coated in order for the substrate to be coated with the doped glass layer by means of plasma ion assisted deposition (PIAD).

If it is desired to produce a patterned luminescence standard on a substrate, the substrate is first of all provided with a masking by means of a standard masking process, with the masking being at least partially removed again following the coating operation.

Figure 7:
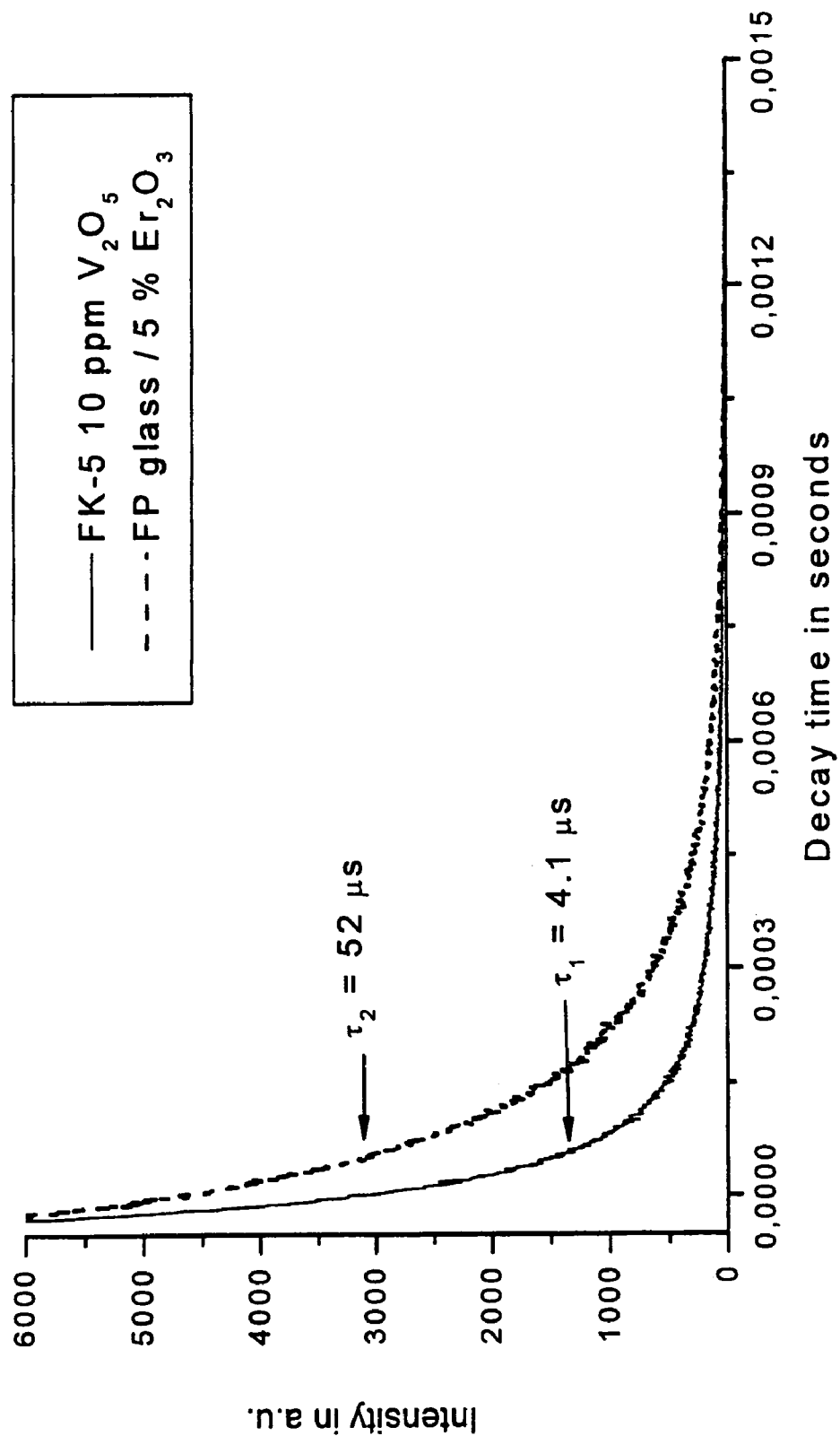
FIG. 7 shows a plot of the decay times of the standard FK-5 doped with 10 ppm of $V_2O_5$ and of FP doped with 5 wt.-% of $Er_2O_3$, with the intensity shown in true units over the decay time in seconds.
Figure 8:
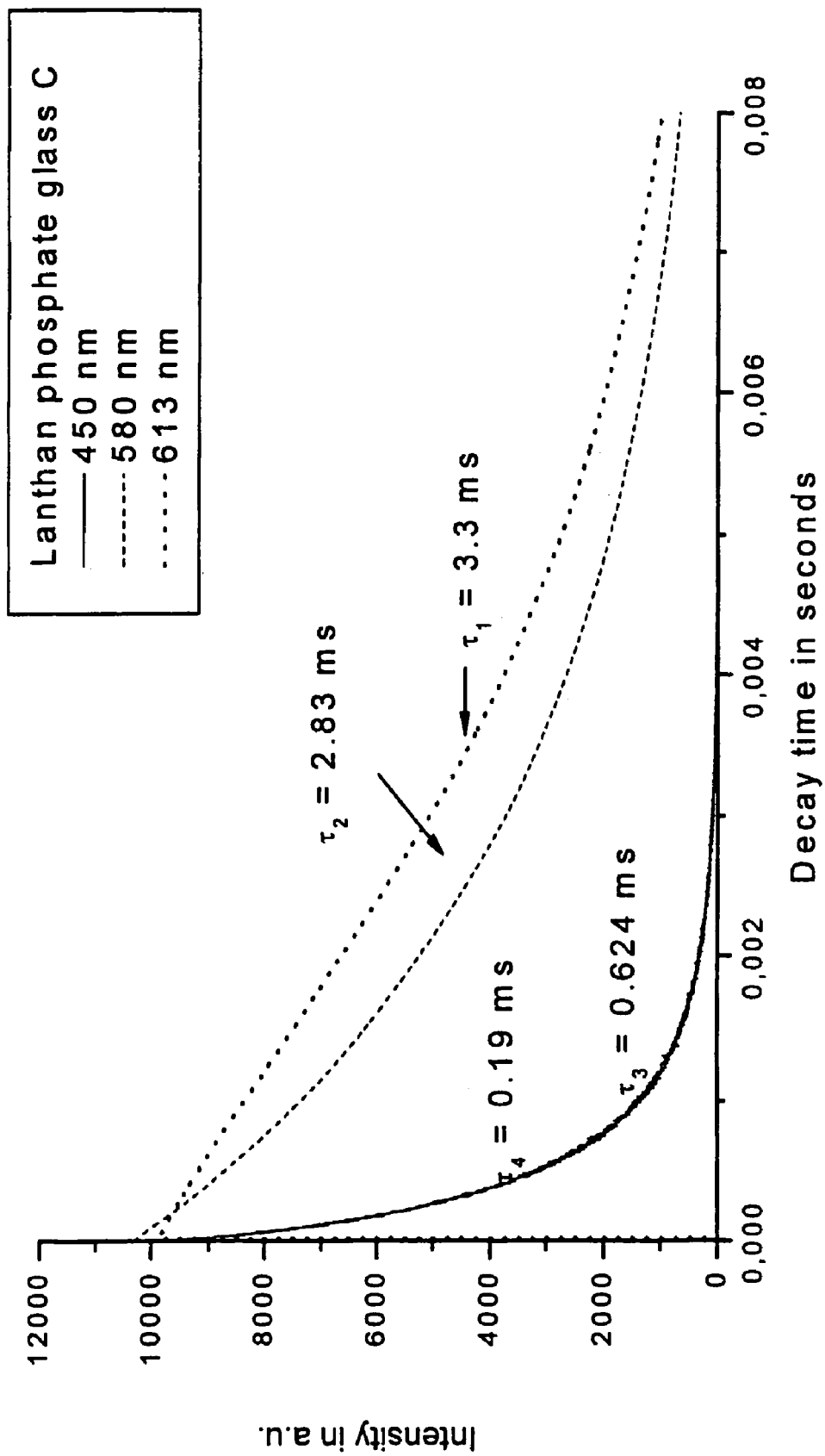
FIG. 8 shows a plot of the decay times of the lanthanum phosphate glass sample C, with the intensity shown in true units over the decay time in seconds.

As a further example the utilization of doped FK and FP glasses as decay or lifetime standards is shown in FIG. 7. The glasses FK-5 (FK51/FK52 see Tab. 2) doped with 10 ppm of $V_2O_5$ and FP doped with 5 wt.-% of $Er_2O_3$ (see example 2) are shown in FIG. 7.

Decay times within several microseconds and milliseconds are observed with dopings with rare earth ions and nonferrous heavy metals.

The decay time was determined as the time at which the maximum intensity has reduced to half its original value.

From FIG. 7 thus decay times of 4.1 microseconds (FK-5 doped with $V_2O_5$) and of 52 microseconds (FP doped with $Er_2O_3$) are observed.

The glasses disclosed herein are characterized in that the decay times are independent from the doping level up to dopings which are smaller than 500 ppm. At doping levels larger than 0.1 wt.-% the decay time depends on the doping level and on the glass matrix. When knowing the respective dependencies a calibration is possible.

For an application as a device standard it is important to take into account the different sensitivities. This may be done by using different doping levels. However, in this case it must be ensured that the intensity is scaled linearly depending on the doping level.

Figure 9:
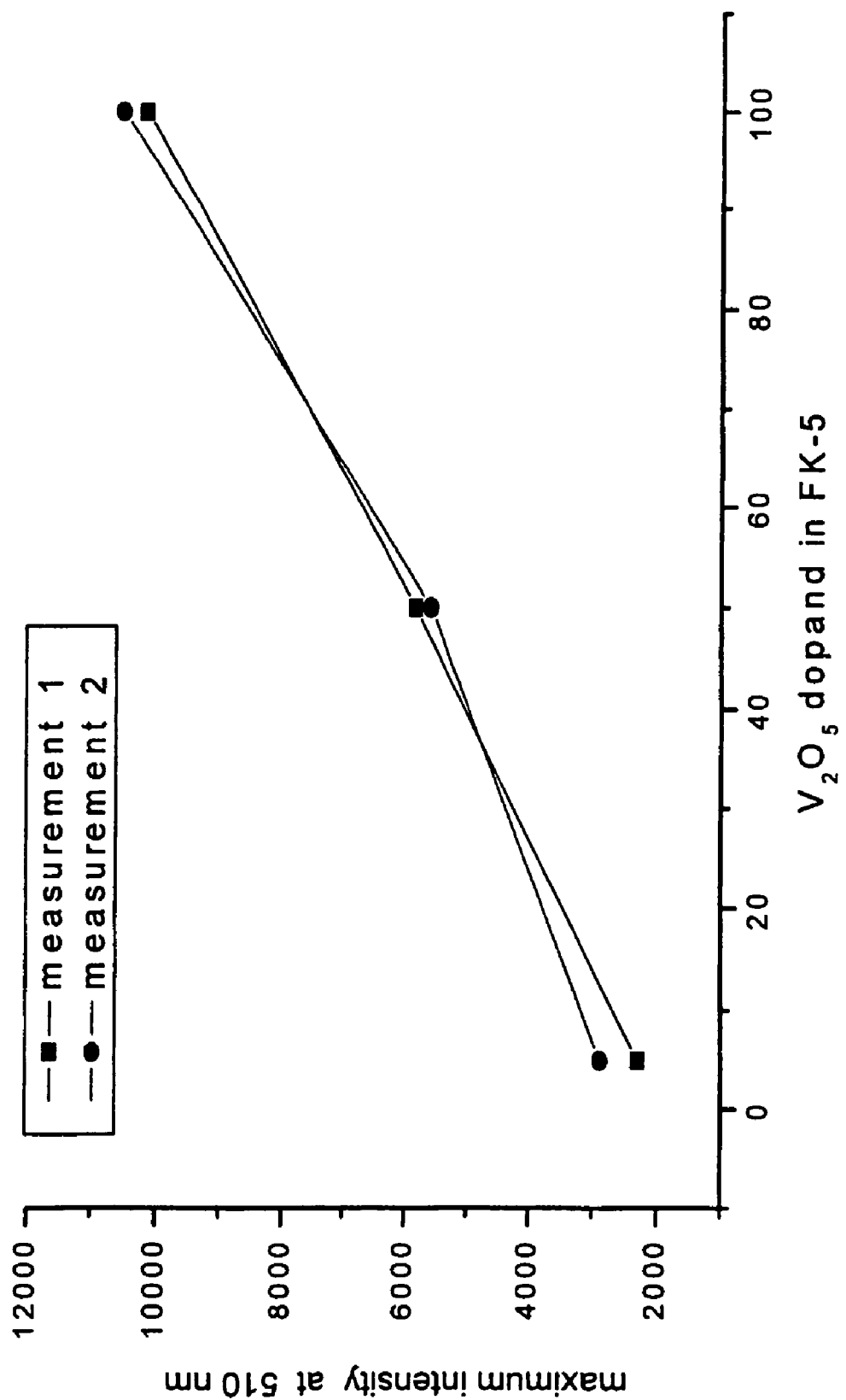
FIG. 9 shows the maximum intensity of the emission at 510 nm for FK-5 depending on the doping with $V_2O_1$, between 10 and 100 ppm, shown for two independent measurement sequences.

In FIG. 9 the maximum intensity of the emission at 510 nm is shown for FK-5 doped with 10 ppm of $V_2O_5$. The maximum intensities are shown for to independent measurement sequencies.

Finally standards must also have a long time stability, i.e. the emission must not vary by more than 5 to 10% over a two-year period of time.

Figure 10:
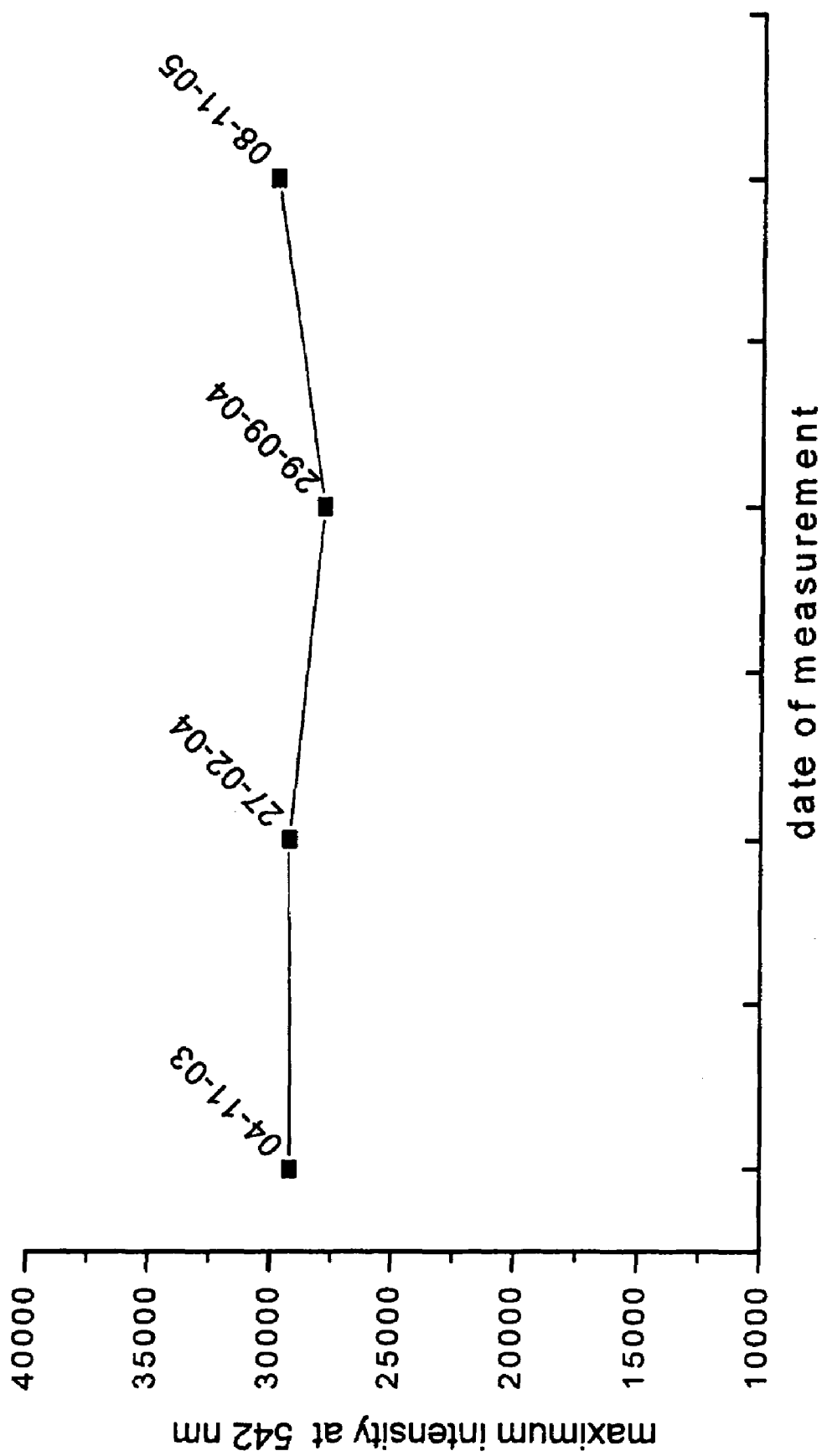
FIG. 10 shows the long time behavior of the lanthanum phosphate glass (sample C) for the emission intensity at 542 nm.

In FIG. 10 the long term stability of the lanthanum phosphate glass sample B (see Tab. 1) is shown for the emission at 542 nm.

It can be seen that the variation of the intensity is smaller than 5% for a time period of 2 years.

To demonstrate the homogeneity or the invariance of the fluorescence characteristics, respectively, with respect to the place of sample extraction from the glass block, a total of 18 samples (shaped as cells of 10×10×40 mm³) were extracted from a sample of the lanthanum phosphate glass A and tested. The result at an excitation of 550 nm and of 613 nm is shown in FIGS. 11 and 12.

Figure 11:
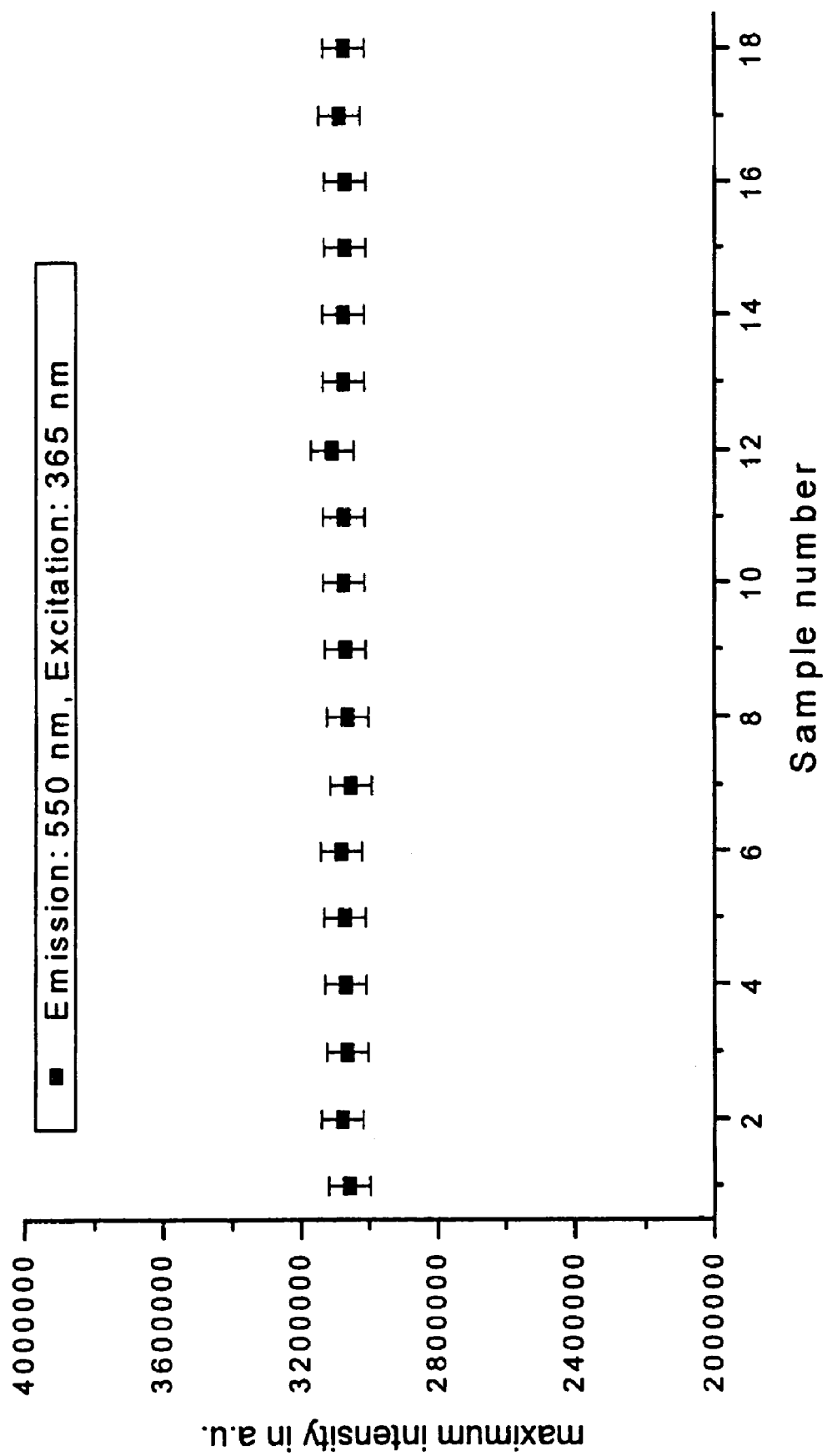
FIG. 11 shows the result of homogeneity tests with respect to the maximum intensity at 550 nm for a total of 18 samples taken from different locations from the same glass block of the lanthanum phosphate glass A.

FIG. 11 shows the maximum emission at 550 nm with excitation at 365 nm. It can be seen that the maximum intensity does not vary by more than 2% from sample to sample.

Figure 12:
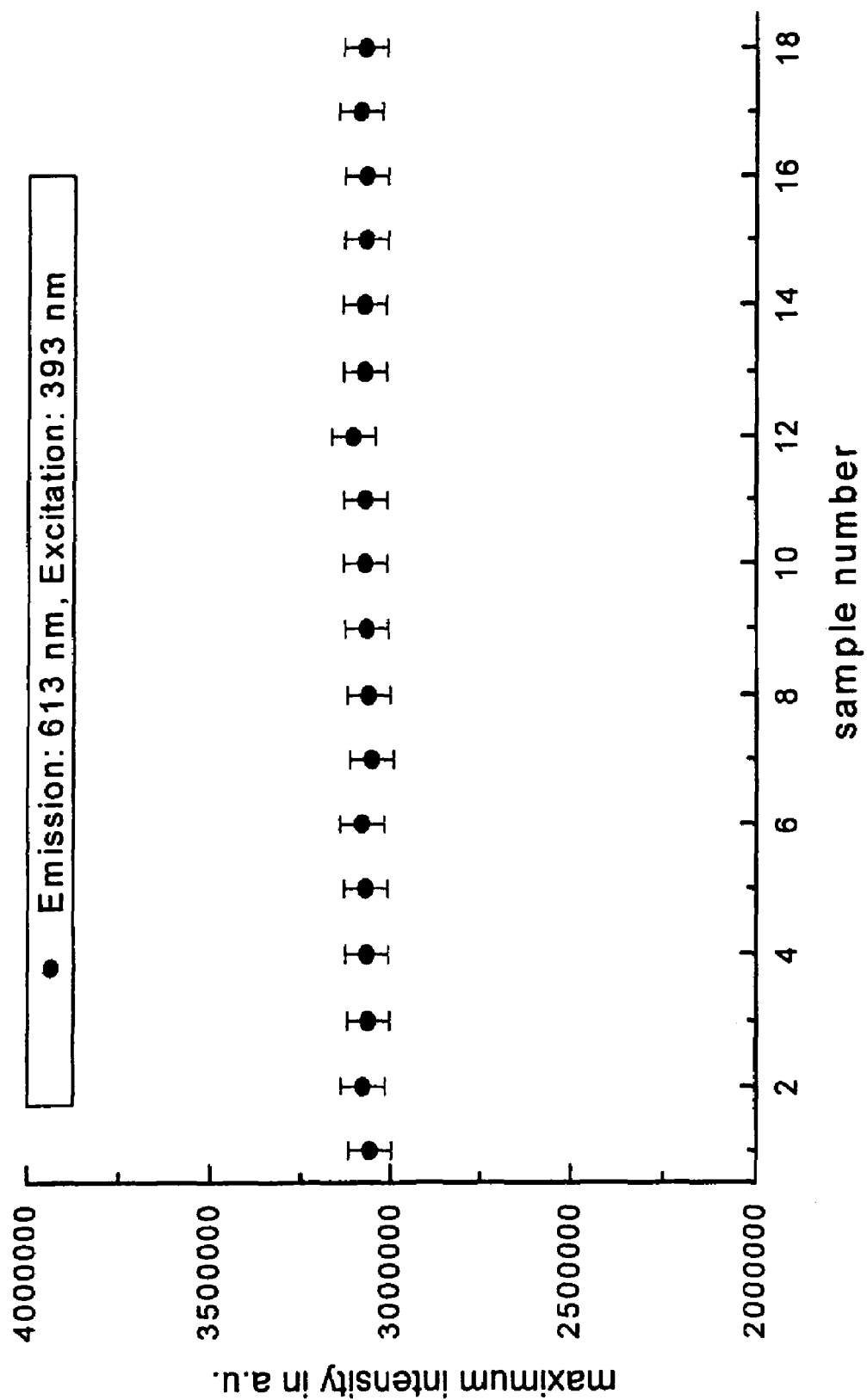
FIG. 12 shows the result of homogeneity tests with respect to the maximum intensity at 613 nm for a total of 18 samples taken from different locations from the same glass block of the lanthanum phosphate glass A.

Similar results are reached with respect to the emission at 613 nm with excitation at 393 nm shown in FIG. 12. The excitation at 393 nm means that the transition f-f of the $Eu^{3+}$, is excited selectively. Herein the variations are even smaller than 1%.

Figure 13:
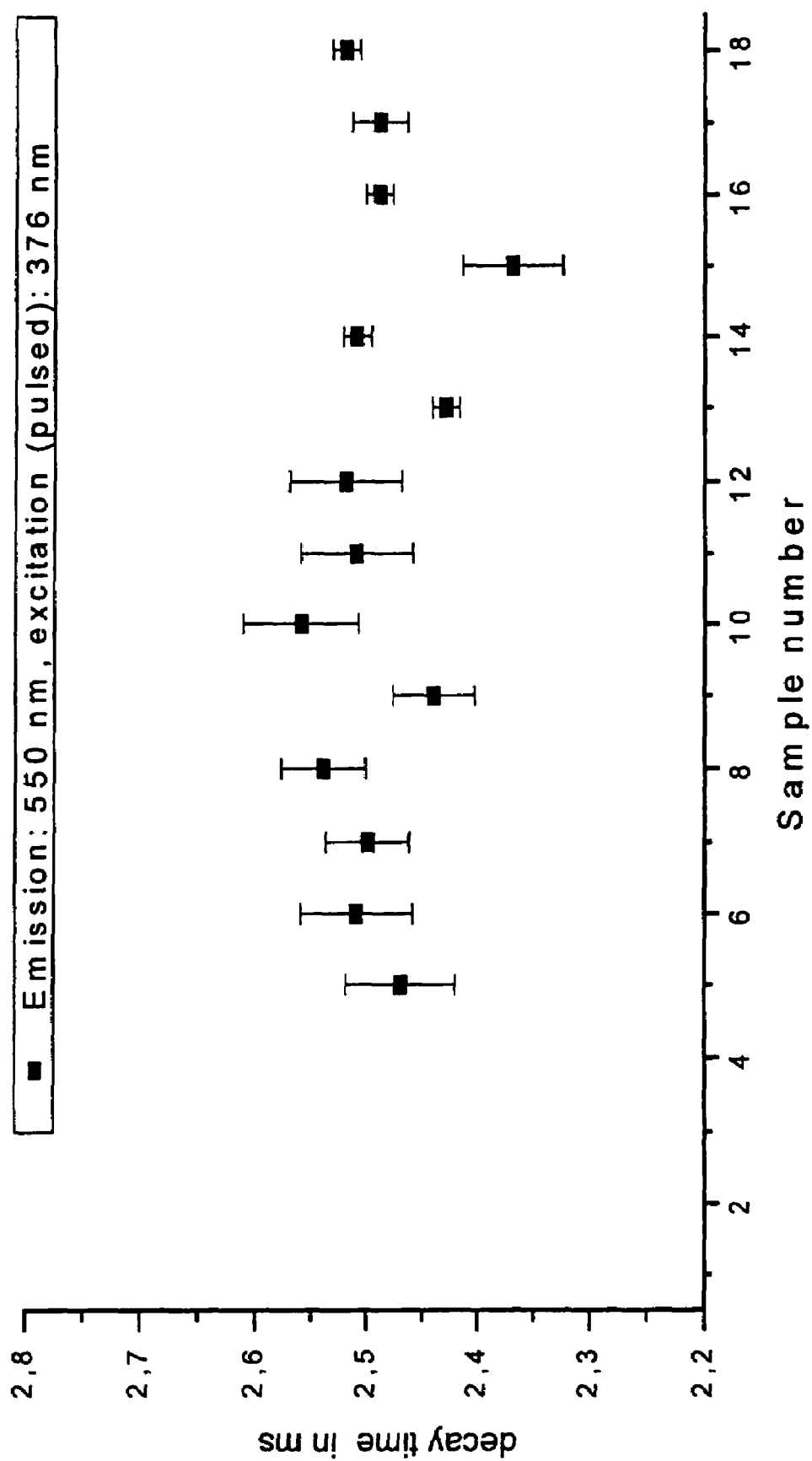
FIG. 13 shows the variation of decay times at 550 nm for samples taken from different locations of the same glass block of lanthanum phosphate glass A.
Figure 14:
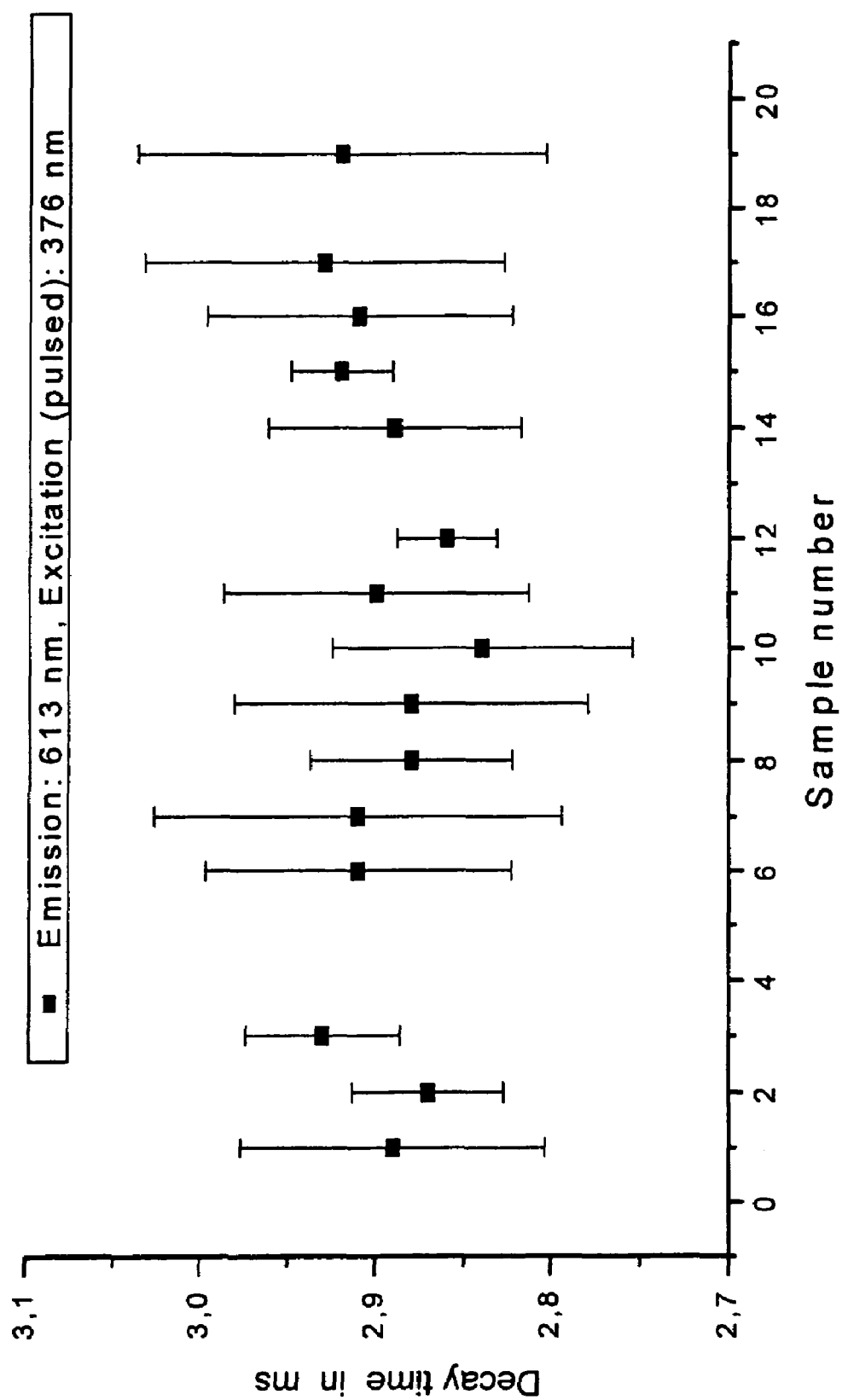
FIG. 14 shows the variation of decay times at 613 nm for samples taken from different locations of the same glass block of lanthanum phosphate glass A.

An even more sensitive demonstration of the homogeneity can be made by determining the decay time for the respective emissions at 550 nm and at 613 nm which is shown in FIGS. 13 and 14. The measurement was made by the so called single-photon-counting-detection (TPCD) method, according to which the single emitted photons are counted and displayed depending on time of the pulsed excitation. Pulsing was effected using a LED having a maximum emission at 376 nm.

In both cases it can be seen that the decay times are between 2.3 and 2.6 milliseconds for 550 nm and between 2.8 and 3.0 milliseconds, respectively, for 613 nm. The relative deviations are smaller than 5% and are within the accuracy of measurement of the equipment used.

Thus according to the invention standards for referencing luminescence measurements are disclosed that have one or more of the following characteristics:

(a) a decay time independent from the doping level up to a doping of 500 ppm;

(b) a variation of the maximum intensity by 10% or by even 5% over a time period of two years;

(c) a homogeneity of the samples depending on the location of the sample extraction which is smaller than 3%, or even smaller than 2%, or even on the order of 1%;

(d) a variation of the decay times depending on the location of extraction on the order of 10% or even on the order of 5% or less.

The invention claimed is:

1. A standard for referencing luminescence signals, comprising an optically transparent base material, said base material being a lanthanum phosphate glass;

said base material further comprising a bulk doping with at least one luminescent component selected from the group formed by a rare earth and a nonferrous metal, wherein said bulk doping comprises at least one component selected from the group formed by cobalt, chromium and manganese; and further wherein said base material is a lanthanum phosphate glass comprising (in wt.-% based on oxide content):

$P_2O_5$ 30 to 90
$La_2O_3$ more than 0 up to 30
$Al_2O_3$ 0 to 20
$R_2O$ 1 to 20
refining agents 0 to 3,
wherein R is at least one element selected from the group formed by the alkali metals.

2. The standard of claim 1, wherein said base material is a lanthanum phosphate glass comprising (in wt.-% based on oxide content):

$P_2O_5$ 50 to 80
$La_2O_3$ 5 to 20
$Al_2O_3$ 5 to 15
$R_2O$ 1 to 20
refining agents 0 to 3,
wherein R is at least one element selected from the group formed by the alkali metals.

3. The standard of claim 2, wherein said base material comprises 5 to 15% by weight of $K_2O$.

4. The standard of claim 2, wherein said bulk doping comprises 0.01 to 5% by weight of at least one dopant selected from the group formed by $Cr_2O_3$, $Ce_2O_3$, $Eu_2O_3$, $Tb_2O_3$, $Er_2O_3$ and $Tm_2O_3$.

5. The standard of claim 4, wherein said base material is doped with from 0.05 to 0.3% by weight $Er_2O_3$ and 0.5 to 2% by weight of $Eu_2O_3$.

6. A standard for referencing luminescence signals, comprising an optically transparent base material, said base material being selected from the group formed by a lanthanum phosphate glass and an optical fluor-crown glass;

said base material further comprising a bulk doping with at least one luminescent component selected from the group formed by a rare earth and a nonferrous metal;
wherein said base material comprises 0.5 to 2% by weight of $La_2O_3$, 10 to 20% by weight of $B_2O_3$, 5 to 25% by weight of $SiO_2$, 10 to 30% by weight of SrO, 2 to 10% by weight of CaO, 10 to 20% by weight of BaO, 0.5 to 3% by weight of $Li_2O$, 1 to 5% by weight of MgO, 20 to 50% by weight of F, and up to 1 wt.-% of refining agents.

7. The standard of claim 6, wherein said bulk doping comprises from 3 to 100 ppm of at least one component selected from the group formed by cobalt, chromium, and manganese.

8. The standard of claim 6, wherein said bulk doping comprises 0.01 to 5% by weight of at least one dopant selected from the group formed by $Cr_2O_3$, $Ce_2O_3$, $Eu_2O_3$, $Tb_2O_3$, $Er_2O_3$ and $Tm_2O_3$.

9. The standard of claim 6, wherein said base material has a water content of less than 0.01% by weight and is prepared from raw materials containing less than 100 ppm of rare earths.

10. A standard for referencing luminescence signals, comprising an optically transparent base material;

said base material further comprising a bulk doping with at least one luminescent component selected from the group formed by a rare earth and a nonferrous metal, wherein said base material is an optical glass which comprises 30 to 60% by weight of $La_2O_3$, 30 to 50% by weight of $B_2O_3$, 1 to 5% by weight of $SiO_2$, 1 to 15% by weight of ZnO, 2 to 10% by weight of CaO, and up to 3 wt.-% of refining agents.

11. A standard for referencing luminescence signals, comprising:

a substrate made of a material which is substantially non-luminescent;
a coating made of an optically transparent base material being selected from the group formed by a glass and a glass-ceramic, and including a doping with at least one luminescent component, wherein said coating is a vaporized and subsequently deposited material comprising said base material and said doping on said substrate.

* * * * *